US005736314A

United States Patent [19]

Hayes et al.

[11] Patent Number: 5,736,314

[45] Date of Patent: Apr. 7, 1998

[54] INLINE THERMO-CYCLER

[75] Inventors: Donald J. Hayes, Plano; David B. Wallace, Dallas; Christopher J. Frederickson, Little Elm, all of Tex.

[73] Assignee: MicroFab Technologies, Inc., Plano, Tex.

[21] Appl. No.: 558,986

[22] Filed: Nov. 16, 1995

[51] Int. Cl.$^{6}$ .......... C12M 3/00

[52] U.S. Cl. .......... 435/4; 435/286.1; 435/286.5; 138/33; 165/185; 219/201; 219/535; 392/480; 392/482; 436/50; 436/52; 436/55; 422/81

[58] Field of Search .......... 219/535, 201, 219/528; 392/479, 480, 482; 165/185, 182; 435/285.1, 286.5; 138/33; 436/50, 52, 55; 422/81

[56] References Cited

U.S. PATENT DOCUMENTS

| | | | |
|---|---|---|---|
| 3,475,597 | 10/1969 | Desloge | 392/480 |
| 3,887,790 | 6/1975 | Ferguson | 219/535 |
| 4,728,776 | 3/1988 | Vincent | 392/480 |
| 4,735,259 | 4/1988 | Vincent | 392/480 |
| 5,409,586 | 4/1995 | Kamahori et al. | 204/182.8 |

*Primary Examiner*—David A. Redding

*Attorney, Agent, or Firm*—Locke, Purnell, Rain, Harrell; Harry J. Watson

[57] ABSTRACT

Thermo-cycling for biological material is provided by a channel such as a capillary tube extending through a series of temperature control elements. Each temperature control element maintains the adjacent portion of the channel at a desired temperature. Fluid to be processed is introduced into the tube through the inlet and flows, preferably through capillary action, to the outlet. The temperature of the fluid changes as it passes each temperature control element and is thus thermo-cycled through a predetermined sequence of temperatures.

14 Claims, 4 Drawing Sheets

INLINE THERMO-CYCLER

This invention relates to cycling biological materials through desired sequences of temperatures. More particularly, it relates to apparatus for thermo-cycling fluid while the fluid flows through the apparatus and to methods of using such apparatus.

Genetic testing of DNA and related materials is an integral part of clinical, commercial and experimental biology. In the medical field, for example, genetic tests are critical for effective treatment of cancer and inherited diseases. Oncologists use genetic tests to obtain the cytogenetic signature of a malignancy which in turn guides the choice of therapy and improves the accuracy of prognoses. Similarly, monitoring frequency and type of mutations persisting after chemotherapy or radiation therapy provides a quick and accurate assessment of the impact of the therapy. Perhaps the most important application of molecular diagnosis in oncology is the emerging possibility of using anti-sense genetic therapy to fight tumor growth.

Inherited diseases occur when a person inherits two copies of a defective (referred to hereinafter as an allele) version of a gene. Genetic tests can determine which genes and alleles are responsible for a given disease. Once the gene is identified, further testing can identify carriers of the allele and aid researchers in designing treatments for the disease.

Most genetic tests begin by amplifying a portion of the DNA molecule within a sample of biological material. Amplification is made practical by the polymerase chain reaction (PCR) wherein a DNA synthesizing enzyme (polymerase) is used to make multiple copies of a targeted segment of DNA. By repeating the polymerase copying process, many copies of the targeted segment are produced. For example, thirty (30) repetitions can produce over one million (1,000,000) copies from a single molecule.

Thermo-cycling typically begins with heating the sample to about 95° C. to separate the double strands and make them accessible as templates for polymerase replication. Cooling to about 55° C. allows the polymerase initiators (primers) to hybridize with their target DNA segments. Control of the temperature during the hybridization process is critical for accurate hybridization of the primer to the DNA. Heating from about 55° C. to about 72° C. is necessary for efficient performance of the polymerase enzyme. At the appropriate temperature, the polymerase reaction catalyzes the elongation of new DNA complementary in nucleotide sequence to the target DNA. At the end of the elongation reaction, heating the solution to about 95° C. causes the newly-formed double-stranded DNA to separate into single strands, thus providing templates for another round of PCR amplification.

Current thermo-cycling methods are complex, time consuming and expensive. One thermo-cycling device (known as the MJ Research DNA engine) comprises a surface upon which are placed micro-wells and under which rests a thermoelectric block for heating and cooling biological material placed in the wells. However, this device takes about one and one-half (1.5) minutes to perform each cycle, even when using a simplified two temperature format. The device thus requires approximately forty-five (45) minutes to perform a thirty cycle run.

Various devices using capillary tubes can perform a thirty cycle run in from ten to thirty minutes. These devices require loading and unloading samples to and from the tubes, sealing the tubes and then exposing the tubes to forced air heating. When the loading and unloading steps are included, these procedures may consume as much as two hours of laboratory time. These procedures also require relatively skilled technicians who can handle microliter volumes of reagents.

One conventional type of thermo-cycler uses forced water circulation to heat and cool vessels immersed in a water bath. Three or more reservoirs hold water at different temperatures and rapid pumps and valves bring water from the reservoirs into the bath to produce a huge thermal mass which heats or cools the material in the vessels. Another device used in PCR processes (See European Patent No. 381501) utilizes a flexible bag-like structure with an inner system of chambers. The DNA sample and reagent fluids are loaded into the chambers and the bag is placed on a hot plate for thermo-cycling. After thermo-cycling, the bag is squeezed with external rollers to move the fluid into chambers containing detection reagents.

In the prior art methods, a significant amount of thermo-cycle time is consumed by ramp periods wherein the temperature of the biological material is changed from one target temperature to the next. The length of each ramp period is a function of both the thermo-cycling equipment and the volume of material heated. The prior art methods generally require first heating the test chamber which then transfers heat to the material contained therein. The thermal mass of the test chamber and volume of material in the test chamber produces high thermal inertia and poor heat-loss surface area to volume ratios. Furthermore, the reagents used in the procedure are expensive and their volume (even if only in the fifty microliter range) can make the procedure prohibitively expensive.

Prior methods pose further time limitations by typically generating only one thermo-cycle at a time. Thus, processing multiple samples at the optimum thermo-cycle of each requires processing the samples one after the other (serial processing). Serial processing may be accelerated by using multiple thermo-cyclers, but this approach consumes capital, energy and laboratory space.

Multiple DNA samples can be processed simultaneously using parallel processing. The most common parallel processing technique involves grouping several DNA samples together and subjecting them to a common thermo-cycle. However, the common cycle is necessarily a compromise among the optimum cycles and time savings are thus achieved at the expense of quality of results.

In accordance with the present invention, thermo-cycling apparatus is provided which has a channel extending through a plurality of temperature control units. The channel has a fluid inlet at one end and a fluid outlet at the opposite end. A fluid sample of biological material introduced into the channel through the inlet passes each of temperature control units while flowing to the outlet. Each temperature control unit maintains a portion of the channel at a desired temperature. Thus the fluid is thermo-cycled through the desired temperature sequence while flowing through the channel.

The channel is preferably designed to handle small fluid volumes. For example, a capillary tube with its inlet equipped with a conventional fitting to facilitate automated loading of unprocessed fluids is suitable. The outlet may be equipped with a conventional fitting for connecting to a storage or analysis channel or tube for collecting the processed fluid. The temperature control units are preferably thermoelectric modules arranged in a linear array and positioned in thermal contact with the fluid channel. Because of the size of the tube used, the quantity of expensive reagents needed can be minimized. The ramp periods between each thermo-cycle target temperature are substantially reduced because of the small fluid volume. Direct discharge into the analysis chamber reduces the number and complexity of steps which must be performed by technicians. Since the apparatus may include multiple, independently controllable, inline thermo-cycling devices, multiple material samples can be processed simultaneously, all at their optimum thermo-cycles. Various other features and advantages of the invention will become more readily understood from the following detailed description taken in connection with the appended claims and attached drawing in which:

The invention is disclosed herein by showing various examples of how the invention can be made and used. Like reference characters are used throughout the several views of the drawing to indicate like or corresponding parts.

Figure 1:
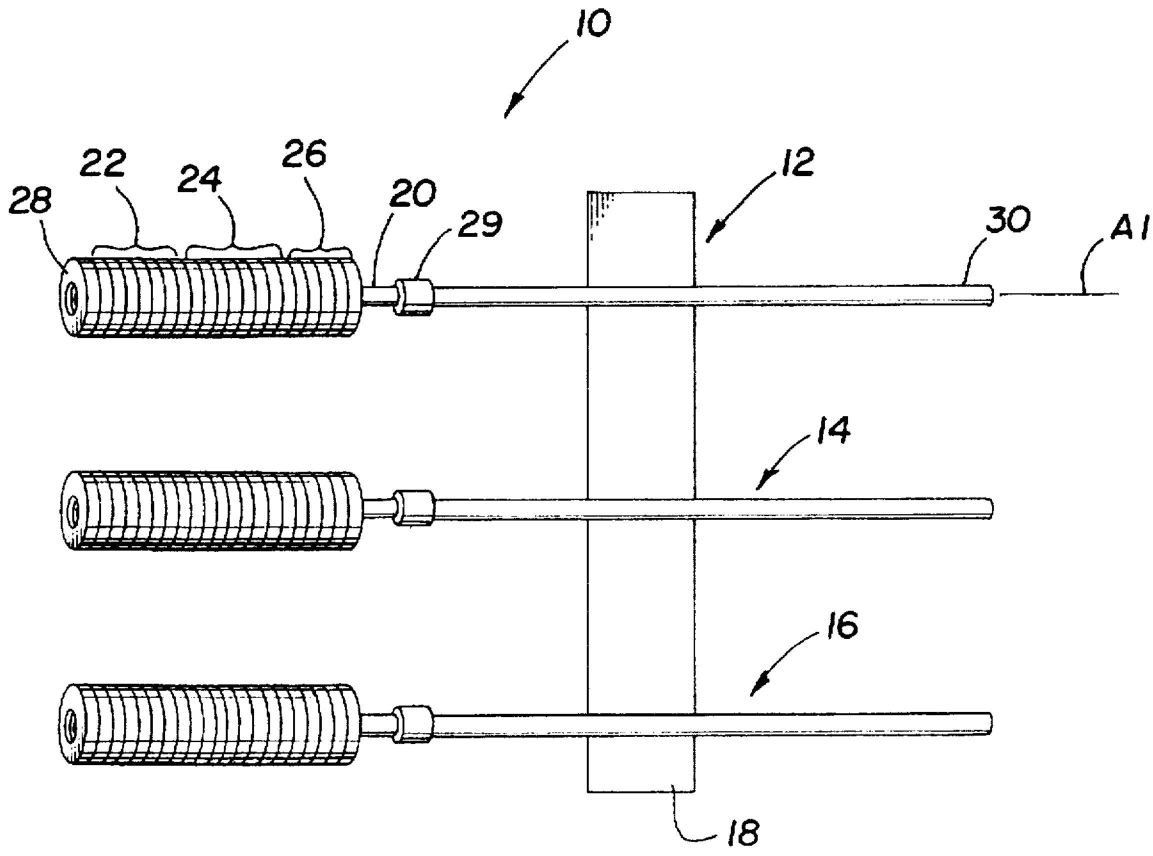
FIG. 1 is a perspective view of apparatus employing the preferred embodiment of the invention.

In FIG. 1 the reference character 10 generally refers to apparatus comprising three inline thermo-cycling devices 12, 14 and 16, all of which are secured together in a base 18. The base is preferably large enough to hold from one (1) to two hundred and fifty six (256) devices but may be large enough to hold a greater number of devices if desired.

Inline device 12 is generally illustrative and comprises an elongated fluid channel or capillary tube 20 extending through three temperature control units 22, 24 and 26. The number of control units used will depend, of course, on the desired thermo-cycle sequence. The device 12 also has an inlet fitting 28, outlet fitting 29, and a storage or analysis channel or tube 30. Alternatively, the fluid channel may be positioned adjacent or only partially enclosed by the temperature control units.

Figure 2:
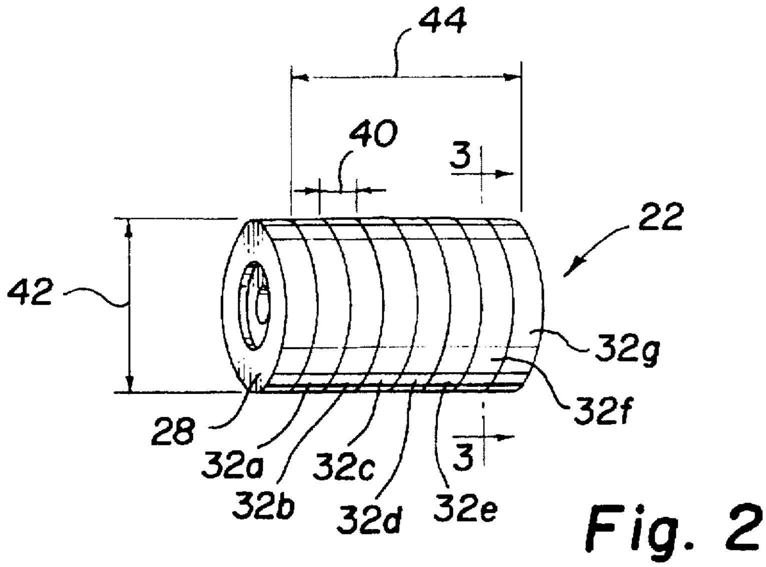
FIG. 2 is an enlarged perspective view of one temperature control unit as shown FIG. 1.
Figure 4:
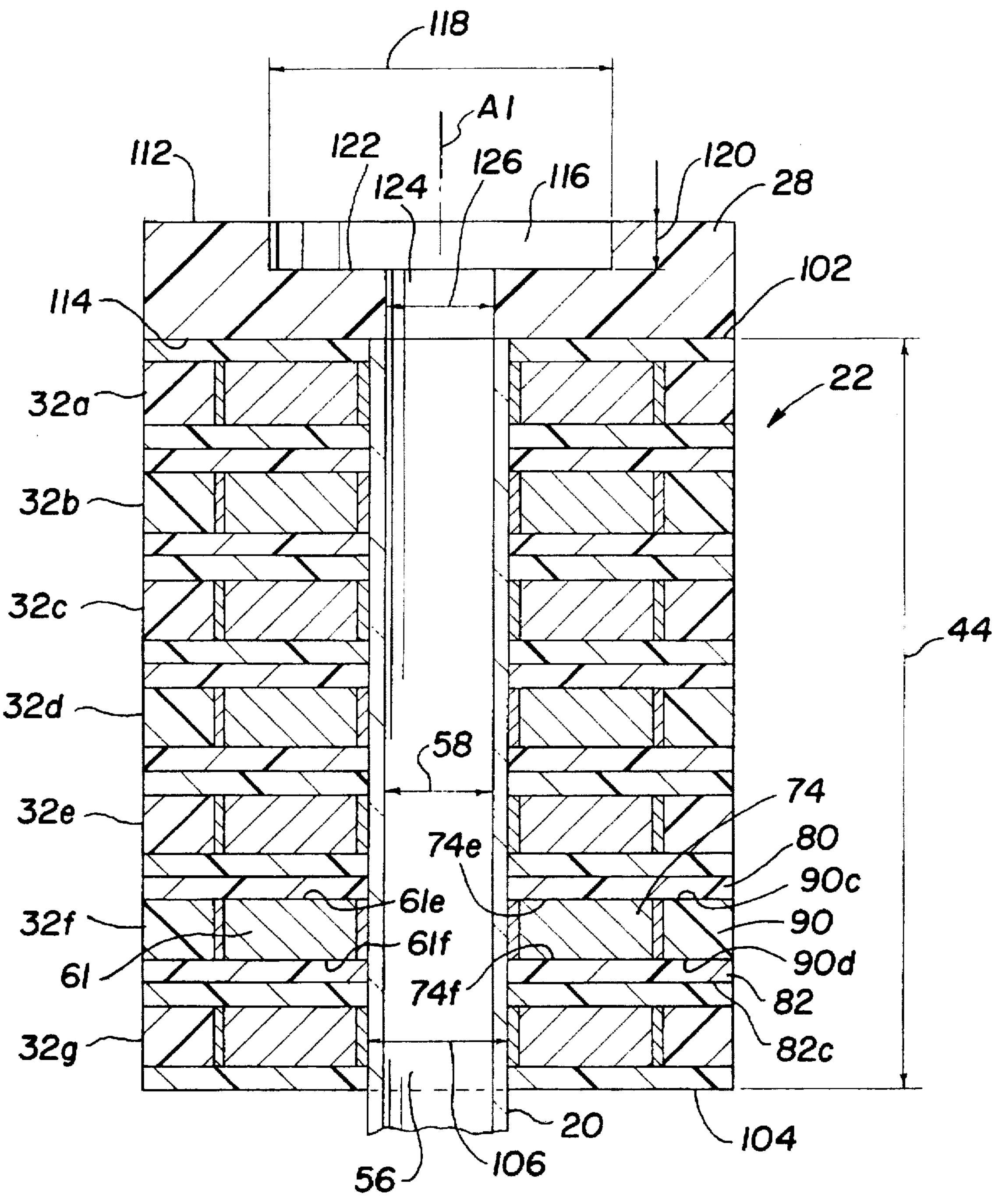
FIG. 4 is a sectional view of a thermoelectric module taken along line 4—4 of FIG. 2.

Control unit 22 is generally representative of control units 24 and 26 and is shown in greater detail in FIGS. 2 and 4. Control unit 22 (as illustrated) comprises seven (7) thermoelectric modules **32*a*–32*g*. Each module has a thickness 40 and a diameter 42. The thickness and diameter will typically be the same for each module but may vary if desired. The modules are positioned adjacent each other in a linear fashion to form the control unit which has a length 44**. Any desired number of modules can be used to form control units of desired lengths.

Figure 3:
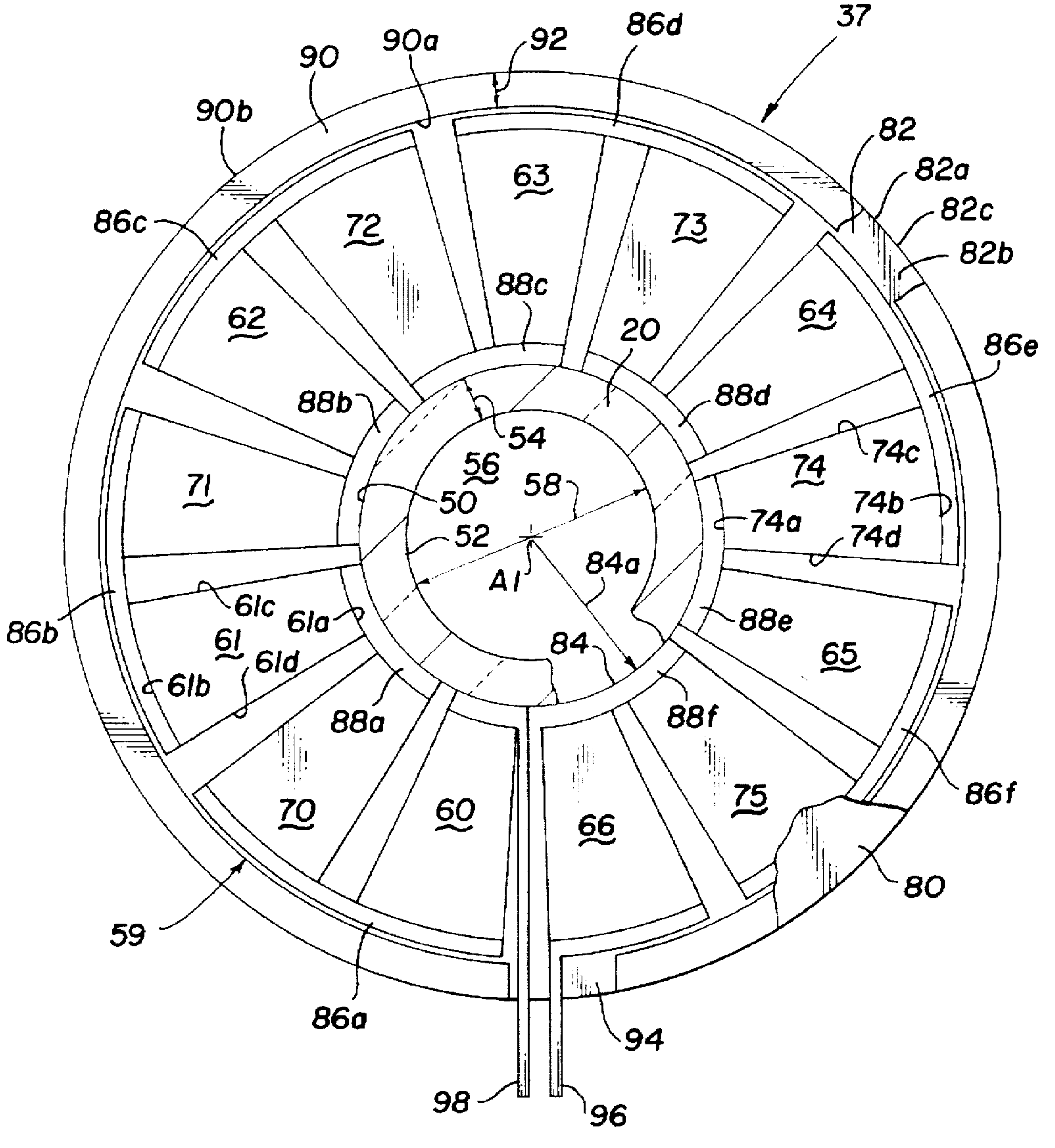
FIG. 3 is a sectional view of a thermoelectric module taken along line 3—3 of FIG. 2.

The construction of thermoelectric module **37*f* is illustrative of the other modules and is shown in greater detail in FIGS. 3 and 4. Module 32*f* preferably comprises N-type and P-type semiconductor materials but may be suitable dissimilar metallic materials. The thermoelectric materials are formed into blocks which are circularly arranged around a tube 20 constructed from electrically insulating material such as glass. The tube 20 has an exterior surface 50 and an interior surface 52 defining a tube wall thickness 54 therebetween. The interior surface defines an internal fluid passage 56 having a diameter 58 (FIG. 3**). While the cross-sectional configuration shown is circular, the fluid passage may have other configurations if desired. For example, a channel having a thin rectangular cross-section (not shown) may be used to increase the heat transfer surface area.

Module **32*f* comprises at least one circular row 59 (FIG. 3) of N-type blocks 60–66 and P-type blocks 70–75 sandwiched between upper and lower plates 80 and 82 (FIG. 4). Block 61 is illustrative of the other N-type blocks and has an internal surface 61*a*, external surface 61*b*, side surfaces 61*c* and 61*d*, and upper and lower surfaces 61*e* and 61*f*. Block 74 is illustrative of the other P-type blocks and has internal surface 74*a*, external surface 74*b*, side surfaces 74*c* and 74*d*, and upper and lower surfaces 74*e* and 74*f***.

Plates 80 and 82 are preferably electrically insulating, thermally conductive material such as polyamide or the like. As shown in FIG. 3, plate 82 has an outer perimeter **82*a* and upper and lower surfaces 82*b* and 82*c*. The plate also has a centrally located hole 84 with a radius 84*a* as measured from axis A1 to accommodate tube 20**.

The N-type and P-type blocks are arranged in sequentially alternating order on upper surface **82*b* of plate 82 with their internal surfaces facing the capillary tube 20. The number of blocks shown is for illustrative purposes only. Module 32*f* may have a greater or fewer number of blocks if desired. Each block is electrically connected to the adjacent blocks by conductive traces. The traces are preferably metallic material such as copper and may be formed by any suitable process. As shown in FIG. 3 external traces 86*a*–86*f* interconnect the external surfaces of blocks 60 and 70, 61 and 71, 62 and 72, 63 and 73, 64 and 74, 65 and 75, respectively. Internal traces 88*a*–88*f* interconnect the internal surfaces of blocks 70 and 61, 71 and 62, 72 and 63, 73 and 64, 74 and 65, 75 and 76, respectively. The traces may be positioned in alternative arrangements provided the resulting current flow through the blocks results in heat being pumped either toward or away from the capillary tube 20**.

The internal traces are positioned adjacent the exterior surface 50 of tube 20 and provide a thermally conductive path between the tube and the row of blocks 59. The external traces are surrounded by a spacer ring 90 which has internal and external surfaces **90*a* and 90*b* and upper and lower surfaces 90*c* and 90*d*. Internal surface 90*a* is positioned adjacent the external traces and the thickness 92 of the ring extends radially to position exterior surface 90*b* flush with outer perimeter 82*a* of lower plate 82. The spacer ring 90 includes a gap 94 through which terminals 96 and 98** extend. An external power source (not shown) supplies current to the row of blocks through the terminals.

The blocks are connected in series so that current will flow in either direction through the row of blocks depending on the polarity of the current at terminals 96 and 98. Since the traces alternate between the external and internal surfaces on the blocks, the direction of the current flow in each block will be either toward or away from the tube 20 depending upon the direction of the current flow. The module will thus pump heat either toward or away from the tube 20, depending on polarity.

Modules **32*a*–32*e* and 32*g* are constructed similarly to module 32*f* and are arranged with their centrally-located holes in alignment along axis A1. The modules are preferably secured together to form temperature control unit 22. The aligned holes define a cylindrical opening 106 which accommodates the length portion of the tube 20 equal to the length 44** of the control unit.

As shown in FIG. 4 inlet fitting 28 is secured to module first end 102. The fitting includes a first major face 112 adapted for use with automated loading apparatus and a second major face 114. The first major face 112 has a centrally located counter-bore 116 having a diameter 118 and a depth 120. The bottom surface 122 of the counter-bore has a centrally located orifice 124 with a diameter 126 the same size as the internal passage 56 of tube 20.

Figure 5:
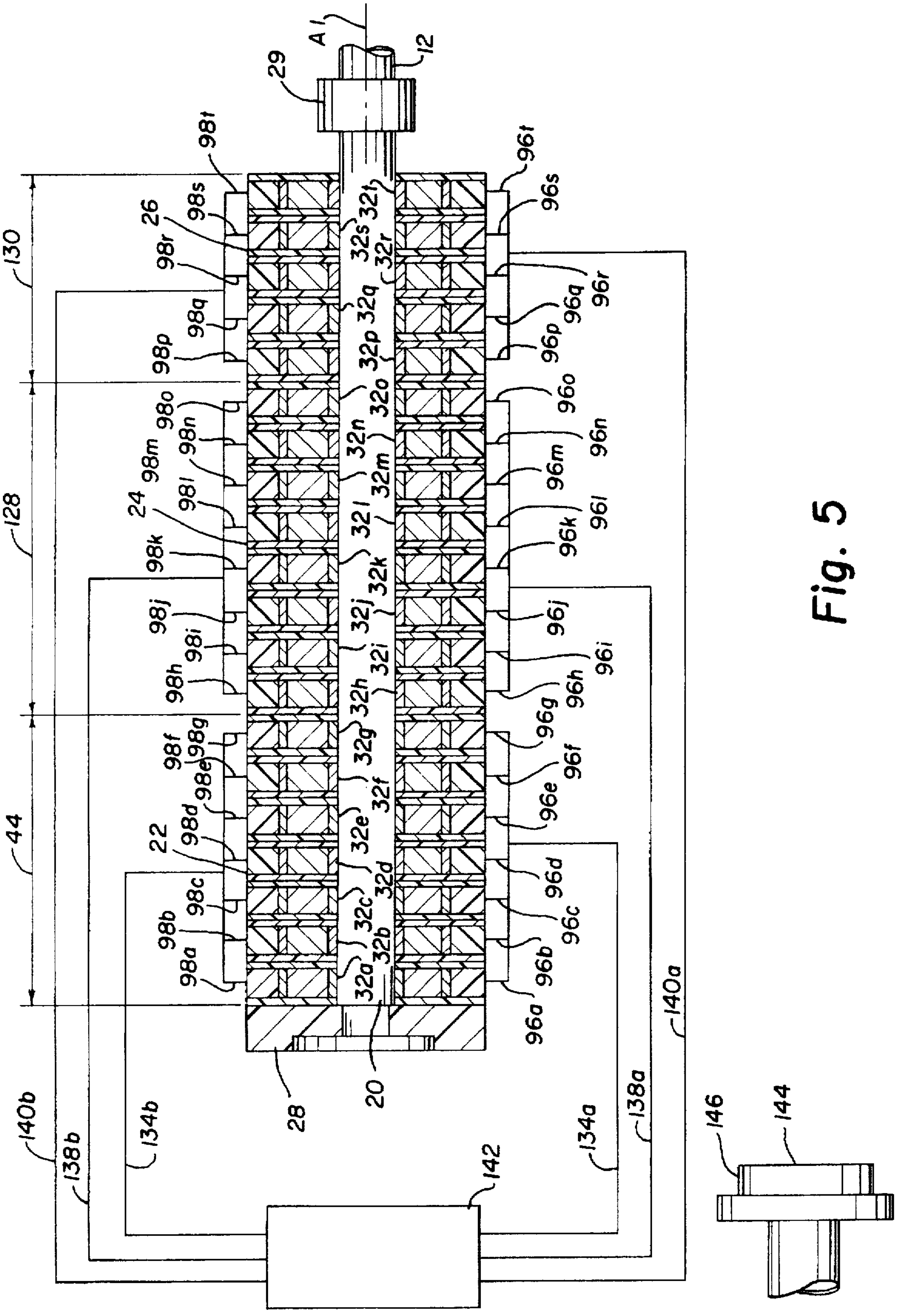
FIG. 5 is a sectional view of a large inline apparatus employing the invention.

FIG. 5 shows the temperature control units 22, 24 and 26 aligned along longitudinal axis A1 and tube 20 extending through their centers. Control unit 22 has seven (7) modules **32*a*–32*g* as previously described and a length 44. Unit 24** has eight (8) **32*h*–32*o* modules and a length 128, and unit 26 has five (5) modules 32*p*–32*t* and a length 130**.

Each pair of terminals extending from the modules is interconnected so that the modules within a control unit are commonly controlled. The connected pairs of terminals **96*a*–96*g* and 98*a*–98*g*, 96*h*–96*o* and 98*l*–98*o*, 96*p*–96*t* and 98*p*–98*t* are represented schematically in FIG. 5. Since the terminal pairs are connected together, control units 22, 24, 26 are operable via connections 134*a*–134*b*, 138–138*b* and 140*a*–140*b*, respectively, to power distributor 142. The power distributor 142** may be any combination of conventional power supplies, polarity switches, programmable controllers, etc.

Conventional loading apparatus 144, having a fitting 146 designed to mate with inlet fitting 28, is used to load unprocessed fluid into the tube 20. The tube 20 is preferably sized to provide a capillary effect for drawing fluid from the inlet fitting 28 to the outlet fitting 29. However, larger tubes or channels may be used and/or the device may rely on pumps or gravity to move the fluid through the tube.

The power distributor 142 maintains control units 22, 24 and 26 at different temperatures. For example, if the fluid is a DNA sample to be amplified using PCR, control unit 22 can be maintained at 95° C., unit 24 at 55° C. and unit 26 at 72° C. Since the control units are in thermal contact with the fluid passage 56, the control units thus maintain a portion of tube 20 extending through their centers at the same temperatures.

Unprocessed fluid is introduced into tube 20 through inlet fitting 28 and drawn toward the outlet fitting 29. As the fluid flows through the length 44 of control unit 22 it is heated to 95° C. As the fluid moves into the length 128 of control unit 24 it is cooled to 55° C. Finally, as the fluid moves into the length 130 of control unit 26 it is heated to 72° C. When the fluid passes through the outlet fitting 29 it has been thermo-cycled through one PCR replication. Additional temperature control units may be provided to repeat the three temperature cycle or to heat and cool the liquid to more than three temperatures.

The length of time a fluid remains at each temperature is a function of both the fluid flow rate and the length of the control unit. The flow rate depends on such factors as the size of the tube, fluid viscosity, temperature and pressure. Apparatus may designed in which these factors cooperate to yield any desired flow rate. The control units must also be designed with the lengths necessary to maintain the fluid at the desired temperature for the desired time period.

Heat transfer between adjacent temperature regions may result in transition regions where the tube is maintained at temperatures other than those necessary to perform the desired reaction. This effect may be controlled by increasing the lengths of the control units by amounts related to the lengths of the transition regions. The transition regions may also be minimized by spacing the control units apart from each other (not shown) or by interposing a thermal insulator (not shown) between adjacent control units.

The processed fluid is discharged from the outlet fitting 29 and flows into outflow channel or capillary tube 12. The outflow capillary may store or transport the processed fluid and may also be used for electrophoretic, fluorimetric or absorptiometric analysis.

From the foregoing it will be recognized that the principles of the invention may be employed in various arrangements to obtain the benefits of the advantages and features disclosed. It is to be understood, therefore, that although numerous characteristics and advantages of the invention have been set forth, together with details of the structure and function of various embodiments of the invention, this disclosure is illustrative only. Various changes and modifications may be made in detail, especially in matters of shape, size and arrangement of parts, without departing from the spirit and scope of the invention as defined by the appended claims.

What is claimed:

1. Apparatus for thermo-cycling a fluid sample of biological material comprising:

(a) at least one elongated channel having a fluid inlet and a fluid outlet; and (b) a plurality of temperature control elements arranged linearly in series and positioned in thermal contact with said at least one elongated channel wherein each temperature control element has the capability of independently heating or cooling a fluid flowing through the channel between said inlet and said outlet to a predetermined temperature above or below the temperature of the fluid when it reaches said control elements.

2. Apparatus as defined in claim 1 wherein said temperature control elements comprise thermoelectric modules.

3. Apparatus as defined in claim 2 wherein said thermoelectric modules encircle said channel.

4. Apparatus as defined in claim 1 including a pump for moving fluid from the inlet to the outlet.

5. Apparatus for thermo-cycling a fluid sample of biological material comprising:

(a) at least one capillary tube having an inlet and an outlet; and (b) a plurality of heating and/or cooling modules arranged adjacent to each other and along said tube, each said module being controllable to maintain a portion of said tube at a desired temperature different from the temperature of the other portions of said tube so that fluid flowing through said tube from the inlet to the outlet may be cycled through a predetermined temperature sequence.

6. Apparatus as defined in claim 5 wherein said heating and cooling elements comprise thermoelectric modules.

7. Apparatus as defined in claim 5 wherein said capillary tube extends through the centers of said heating and cooling elements.

8. Apparatus as defined in claim 5 including an analysis channel in fluid communication with the outlet.

9. A method for thermo-cycling fluid biological material comprising the steps of:

(a) providing a fluid channel having an inlet at one end, an outlet at an opposite end and a plurality of temperature control elements positioned in thermal contact with said channel between said one end and said opposite end;

(b) providing power to each temperature control element to maintain the portion of the channel adjacent each temperature control element at a predetermined temperature which varies from one control element to the next; and (c) introducing a fluid biological material into the channel at the inlet; and (d) flowing the fluid through the channel.

10. A method as set forth in claim 9 including the step collecting the fluid sample in a storage channel connected to said opposite end.

11. A method as set forth in claim 9 including the step of collecting said fluid in an analysis channel connected to said opposite end.

12. A method as set forth in claim 11 including the step of analyzing the fluid sample collected in the analysis channel.

13. Apparatus for thermo-cycling a fluid sample of biological material, comprising:

(a) at least one elongated channel having a fluid inlet and a fluid outlet;

(b) said at least one elongated channel being sized to provide a capillary for drawing fluid from the inlet to the outlet; and (c) a series of temperature control elements positioned in thermal contact with said at least one elongated channel to independently heat and/or cool the channel to desired temperature different from the temperature of other portions of the channel between said inlet and said outlet.

14. Apparatus for thermo-cycling a fluid sample of biological material, comprising:

(a) at least one elongated channel having a fluid inlet and a fluid outlet;

(b) a series of temperature control elements positioned in thermal contact with said at least one elongated channel to independently heat and/or cool the channel to desired temperature different from the temperature of other portions of the channel between said inlet and said outlet; and (c) an analysis channel in fluid communication with the outlet.

* * * * *